United States Patent
Linder et al.

(10) Patent No.: US 6,681,003 B2
(45) Date of Patent: Jan. 20, 2004

(54) DATA COLLECTION AND SYSTEM MANAGEMENT FOR PATIENT-WORN MEDICAL DEVICES

(75) Inventors: Marshal Linder, Pittsbrugh, PA (US); Thomas Kaib, North Huntingdon, PA (US)

(73) Assignee: Lifecor, Inc., Pittsburgh, PA (US)

( * ) Notice: Subject to any disclaimer, the term of this patent is extended or adjusted under 35 U.S.C. 154(b) by 0 days.

(21) Appl. No.: 10/197,159

(22) Filed: Jul. 16, 2002

(65) Prior Publication Data

US 2002/0181680 A1 Dec. 5, 2002

Related U.S. Application Data (63) Continuation of application No. 09/624,275, filed on Jul. 24, 2000.
(60) Provisional application No. 60/157,881, filed on Oct. 5, 1999.

(51) Int. Cl.[7] .............................................. H04M 11/00
(52) U.S. Cl. ................................................. 379/106.02
(58) Field of Search ...................... 379/106.02, 106.01, 379/38, 37, 39, 110.01, 90.01

(56) References Cited

U.S. PATENT DOCUMENTS

| | | |
|---|---|---|
| 4,531,527 A | 7/1985 | Reinhold, Jr. et al. |
| 4,838,275 A | 6/1989 | Lee |
| 5,036,852 A | 8/1991 | Leishman |
| 5,321,618 A | 6/1994 | Gessman |
| 5,367,555 A | 11/1994 | Isoyama |
| 5,390,238 A | 2/1995 | Kirk et al. |
| 5,544,661 A | 8/1996 | Davis et al. |
| 5,594,786 A | 1/1997 | Chaco et al. |
| 5,701,894 A | 12/1997 | Cherry et al. |
| 5,724,025 A | 3/1998 | Tavori |
| 5,730,143 A | 3/1998 | Schwarzberg |
| 5,741,306 A | 4/1998 | Glegyak et al. |
| 5,772,604 A | 6/1998 | Langberg et al. |
| 5,781,442 A | 7/1998 | Engleson et al. |
| 5,974,124 A | * 10/1999 | Schlueter et al. ...... 379/106.02 |
| 6,083,248 A | * 7/2000 | Thompson .................... 607/30 |
| 6,264,614 B1 | 7/2001 | Albert et al. |
| 6,402,691 B1 | * 6/2002 | Peddicord et al. ............ 379/38 |

FOREIGN PATENT DOCUMENTS

| | | |
|---|---|---|
| EP | 0 707 825 A2 | 7/1995 |
| EP | 0 761 255 A1 | 8/1996 |
| WO | WO 97/22297 | 6/1997 |
| WO | WO 98/43537 | 10/1998 |
| WO | WO 99/59465 | 11/1999 |
| WO | WO 00/30529 | 6/2000 |

* cited by examiner

Primary Examiner—Stella Woo
(74) Attorney, Agent, or Firm—Buchanan Ingersoll, P.C.

(57) ABSTRACT

A method and system of monitoring information received from a patient-worn medical device is disclosed. A medical device, such as a portable or implantable device, collects patient and operational information, which information is transmitted to central location, such as a doctor's office or device manufacturer's location. The data collected can be analyzed to monitor both the patient health parameters as well as the operation of the device. Trend analysis can be performed in order for a physician to diagnose the patient's health and a medical device technician can insure correct functioning of the device itself. Communication between the central location and the medical device is preferably done through a modem connection, and software and other updates can be automatically transmitted to the medical device during data download from the device to the central location. Physicians and technicians can access the central location from any home or office computer via the internet.

35 Claims, 6 Drawing Sheets

```
Lifecor Inc. Wearable Cardioverter Defibrillator
Device ID: 1008        Version:
*************************************************************

PATIENT FIRST NAME                         ----------------
PATIENT LAST NAME                          ----------------
PATIENT RESPONSE TEST (AWAKE)              25 SECONDS
PATIENT RESPONSE TEST (ASLEEP)             35 SECONDS
TIME PATIENT GOES TO SLEEP                 00:00 HOURS
TIME PATIENT AWAKENS                       06:00 HOURS
POST TREATMENT PHONE NUMBER                1-800-LIFECOR
MODEM PREFIX (OPTIONAL)
DIALER MODE                                ROTARY
ARRHYTHMIA DETECTION THRESHOLD             150 BPM
PULSE ENERGY #1                            200 JOULES
PULSE ENERGY #2                            MAX. JOULES
PULSE ENERGY #3                            MAX. JOULES
PULSE ENERGY #4                            MAX. JOULES
PULSE ENERGY #5                            MAX. JOULES
 < SET DEFAULTS >    < SAVE >    < EXIT >

Use <TAB> or <BACKSPACE> key to highlight option.
Use <ENTER> key to modify text value.
Use <UP ARROW> or <DOWN ARROW> key to change numeric value.
```

*FIG. 3a*

Patient Address

[Add]    Rercord: 0  Patient: t4s10 xrb 106

| Patient ID | | | | Trial | |
|---|---|---|---|---|---|
| First Name | | M.I. | | Last Name | |
| Birth Date | | SSN | | Race | |
| Status | Active | Sex | | | |
| Address | | | | | |
| Address2 | | | | | |
| Address3 | | | | | |
| City | | | | | |
| State | | Country | | Zip Code | |
| Home Phone | | Other Phone Number | | | |
| Height(cm) | | Weight(kg) | | Chest(cm) | |
| WCD Garment Size | | | WCD Garment Extension | | |

*FIG. 3b*

Patient Adverse Event

| Add | Save | Record: 0 Patient: t4s10 xrb206 |

| First | Prev. | Next | Last |

| Name | | Center | |
|---|---|---|---|
| Date of the event | | | |
| Name of the event | | | |

| Event description | |
|---|---|
| | |

| Was the event caused by WCD? | Unknown relationship ▽ |
|---|---|
| Was the event anticipated? | ⦿ Not Answered  ○ Yes  ○ No |
| Was the event serious? | ⦿ Not Answered  ○ Yes  ○ No |
| Was the event reported to LIFECOR? | ⦿ Not Answered  ○ Yes  ○ No |
| Was the event reported to IRB? | ⦿ Not Answered  ○ Yes  ○ No |
| Was the event reported to FDA? | ⦿ Not Answered  ○ Yes  ○ No |
| Person taking report at LIFECOR | |
| Date report to LIFECOR | |

FIG. 4

| EVENT DATE TIME | EVENT TYPE | TREATMENT | LENGTH |
|---|---|---|---|
| 07/14/1999 11:11:47 | AUTOMATIC | YES | 113 SECONDS |
| 07/14/1999 11:06:41 | BASELINE | N/A | 48 SECONDS |
| 07/14/1999 11:02:00 | AUTOMATIC | YES | 110 SECONDS |
| 07/14/1999 10:56:57 | BASELINE | N/A | 46 SECONDS |

DATA COLLECTION AND SYSTEM MANAGEMENT FOR PATIENT-WORN MEDICAL DEVICES

RELATED APPLICATION

This application is a continuation of patent application Ser. No. 09/624,275 filed on Jul. 24, 2000, which is based on and claims the benefit of our provisional patent application titled, "DATA COLLECTION AND SYSTEM MANAGEMENT FOR PATIENT-WORN MEDICAL DEVICES" filed on Oct. 5, 1999 and assigned Serial No. 60/157,881.

BACKGROUND OF THE INVENTION

1. Field of the Invention

The invention relates generally to patient-worn medical devices, and more particularly, this invention relates to the use of remote transmission and collection of data received from such a device and for the systems management of the device and its components.

2. Description of the Prior Art

Modem medical technology is available for allowing ambulatory patients to function in a normal day to day environment, even while requiring the monitoring of certain health and physical parameters. In addition to this, it is possible to have therapeutic devices or drugs automatically provided to the patient when in time of need. These medical devices are typically worn by the patients to provide the monitoring of a variety of conditions. These devices may also provide for the automatic treatment when the monitoring device detects that such treatment is required. Examples of such devices include a wearable cardioverter defibrillator, cardiac monitors and infusion pumps for the treatment of diabetes. With respect to the wearable cardioverter defibrillator (WCD), an example of such a device is disclosed in U.S. Pat. No. 5,741,306 which issued on Apr. 21, 1998 and its companion continuation-in-part application Ser. No. 09/054,714, filed on Apr. 13, 1998, which patent and application are assigned to the assignee herein and are hereby incorporated by reference in their entirety.

By way of brief explanation, this device provides a patient-worn energy delivery apparatus for imparting electrical therapy to the body of a patient responsive to an occurrence of a treatable condition. The apparatus includes a voltage converter for converting electrical energy from an initial voltage to a final voltage at a plurality of charging rates, and a defibrillator coupled between the converter and the patient so as to impart the electrical energy to the patient. The defibrillator produces preshaped electrical pulses such as defibrillation pulses and cardioversion pulses as determined by the monitoring of the patient. With electrodes appropriately placed on the patient, the device monitors the condition of the patient's heart on a continual basis to determine if the patient requires either a defibrillation pulse or a cardioversion pulse to restore normal heart function.

While the patient may be using any of these various medical devices, it is important that the data collected from the device be analyzed by the care giver. Typically, this means that the patient must travel to the hospital or clinic in order to exchange the device for a different one so that the data collected on that device can be read and analyzed or to at least drop off some sort of memory module, be it either a tape or a paper printout, so that the physician can analyze the data and thus the health of the patient. This necessitates that the patient again travel to the hospital in order to have this procedure done.

Moreover, these devices have traditionally required programming or configuration at the location which originally dispenses the device to the patient who, as stated above, must later return to that center for review of the collected data. When the components of the device need to be upgraded or changed due to expiration of their normal useful life, such as replacement of a battery or any other electronic component such as a solid state memory, the patient again must travel to the dispensing center in order to have this routine maintenance accomplished. Many times such an update to the system merely involves improving or upgrading the system's operating software so that the monitoring and therapy device works in a more efficient and helpful manner.

With digital technology, it is possible for such a device to be able to "download" the data via telephone line, for example, from the patient's home to a remote location. With this type of system, the patient data is collected into a solid state memory which can then be transmitted via telephone line and modem to the hospital or physician's office for analysis of the data by the physician.

It would be advantageous, therefore, if the frequency of the number of trips that the patient must make to the dispensing center, such as a hospital or physician's office, is minimized. Remote transmission of patient data and diagnostic information related to the operation of the device would help eliminate some of the heretofore repetitive trips that the patient must make. Moreover, remote upgrading of the operation of the device would more efficiently aid use of the most therapeutically effective device being available to the patient as quickly as possible.

It is therefore an object of the present invention to provide a medical device which can be worn by a patient and provides for interactive transfer of data and information from the device to a remote center, such as the doctor's office, for monitoring of the patient and of the equipment itself.

A further object of the present invention is to provide a device which can be upgraded remotely from the device dispensing center in order to reduce the number of personal visits by the patient to the dispensing center.

It is a still further object of the present invention to provide a patient-worn medical device which has the capability to transfer information and data with a remote center via telephone dial-in access, direct internet access or radio frequency communications.

SUMMARY OF THE INVENTION

The above and objects are attached by the present invention, according to which, briefly stated, method of monitoring patient medical information, the method comprising the steps providing a wearable medical device for monitoring predetermined patient medical information. In one embodiment, the wearable medical device is a wearable cardiac defibrillator and monitor.

The wearable medical device is operatively connected to the patient and the predetermined patient medical information is recorded in a storage means of the wearable medical device. An outlet port of the wearable medical device is operatively connected to a communications system in order to transmit the predetermined patient medical information to a health care provider by means of the communications system, and the patient medical information recorded in an information database. Access to the patient medical information is provided to predetermined individuals, such as medical personnel for monitoring the patient's health and/or technical personnel for monitoring correct operation of the device.

Where the wearable medical device is a cardiac defibrillation device, the step of recording the predetermined patient medical information comprises recording electrocardiograms of the patient's heart rhythm.

In a system for monitoring patient medical information, the system comprises a medical device operatively attached to a patient for monitoring and storing predetermined medical parameters. The medical device is connected to a communication network, which in turn is connected to the medical device thereby operably connected to exchange information with the patient database, and/or technical personnel for monitoring and upgrading the performance of the device.

BRIEF DESCRIPTION OF THE DRAWING

Various other objects, features and advantages of the invention will become more apparent by reading the following detailed description in conjunction with the drawings, which are shown by way of example only, wherein:

FIG. 3, consisting of FIGS. 3A and 3B, is a representation of computer screen for inputting patient data and various medical information;

DETAILED DESCRIPTION OF THE PREFERRED EMBODIMENTS

Figure 1:
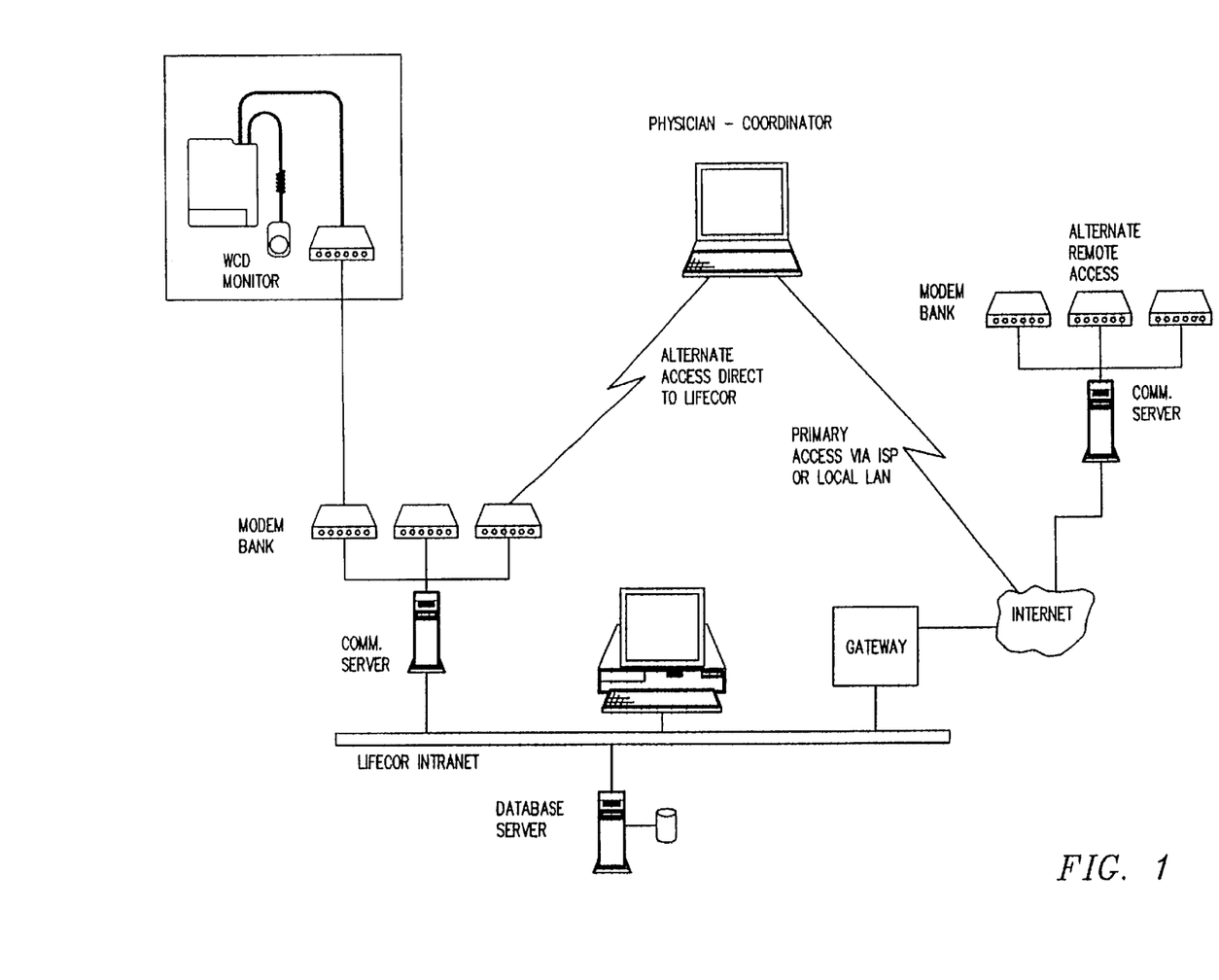
FIG. 1 is an overall schematic diagram of the interconnected data transfer and remote access modules of the present invention.

Referring now to the drawings in detail, FIG. 1 shows an internet based data management architecture for the remote data collection and system management for patient-worn medical devices. The invention employs the use of data modems which employ a variety of transmission vehicles, such as wired telephones, radio frequency transmissions through dedicated or cellular networks or infrared transmission, for example, to provide for data collection and management of a patient-worn device. The internet or other data network is used to make this data available to physicians and their staff, making it possible to review the data from any location and manage the use of the device. Passwords, encryption and other security devices allow control of the data and to provide for patient privacy. In this manner, data need only be sent from the monitoring device to one location or the web server, which location can then be accessible by physicians or device technicians from any location to review the data collected to ensure both the health of the patient and the proper operation of the patient-worn device.

Preferably, the information for the operation of the device is collected at a central location, such as a performance analysis and post market surveillance operation which is maintained by the equipment manufacturer. Remote, dial-in access is available to this central location by both the patient, physician and device maintenance personnel. The patient can download both the patient monitored data as well as operations data for the device to this central location which can be accessed by the physician and/or the maintenance personnel. In addition, the physician can access this data from anywhere by using a common Internet web browser to access the central location via the Internet. The physician can monitor the patient's health data which has been downloaded from the patient-worn device, for example, electrocardiogram (ECG) data. Additionally, since device performance data can be downloaded from the central location, the correct operation of the patient-worn device can be monitored to ensure that the physician is receiving and analyzing proper patient health information.

In this manner, a variety of data collection features can be provided. These include the automatic or manual transmission of sensor data, such as ECG signals from a holter monitor, for example, for collection of data in a database which is preferably a relational database for review and analysis over the course of the monitoring of the patient. In addition, the patient can be prompted for the manual transmission of data either on a predetermined basis or if the physician determines that a particular event has been detected where additional information is required. The use of dedicated modems or industry standard protocols such as TCP/IP allows the use of commercial networks for transmission, which networks can be protected from unauthorized review of information via passwords, encryption or other security devices. In addition, automatic or manual transmission of equipment performance data such as battery status, system faults or failures, capacity, treatment provided and sensor function can be presented to the central location for proper analysis. Automatic or manual transmission of results of analysis performed on the collected data, such as review of arrhythmia events, can then also be provided back to the patient or other physicians. If it is determined that a message is to be sent to the patient prompting him or her to perform certain functions in order to correct any nonconformities that a physician or maintenance personnel detects, automatic or manual transmission of patient compliance and use data can also be sent back to the central location for review by the physician or maintenance personnel to ensure that the patient has complied with whatever instructions either of these groups may have provided.

For example, if it is determined through review and analysis of ECG signals received from patient, that the garment has not been properly positioned such as through excessive "noise" in the ECG signals, a message can be sent to the patient advising him or her that the garment needs adjustment in order to insure proper placement of the electrodes. "Noise" can also be generated by physical characteristics of a particular patient such as body shape, how the electrodes are positioned, and body size. Also, by reference to FIG. 6, the average wear time data for which the patient has worn the device can be analyzed to determine patient compliance. In this way, it is a complete medical profile and information can be received from the patient for analysis by the physician and/or maintenance personal to insure the health of the patient as well as the correct operation of the device.

In the event that it is determined that the device is not operating properly, even though the patient is wearing it properly and for the prescribed period of time, the data can be analyzed and patient parameter changes, such as wear-time recommendations and placement of electrodes, can be implemented for the proper operation of the device for that particular patient. Through the on-line data collection system of the present invention, software upgrades can be transmitted directly to the patient's device during a data download for example, or the patient can be instructed to implement hardware upgrades during his or her next visit to the physician. Also, periodic battery replacement and charging instructions can be given to the patient to insure proper operation of the device. Data received from a multitude of patients can be analyzed to develop trends in device operation for future product improvements or enhancements.

In order to download the data, the patient-worn medical device, such as the WCD, can be connected to an external modem for telephonic connection to the central location. Alternatively, the device may include an internal modem and associated jack for connection to any standard phone line. The device can be programmed to include the appropriate telephone number of the central location. Once the device modem has been connected to the phone line, the patient need only initiate a data send function which can initiate the dialing and remote connection procedures. When connection is established between the patient-worn device and a web server at the central location, the data can be downloaded to that site for retrieval by the patient's physician and/or technical personnel for analysis of the data. Alternatively, direct internet access or radio frequency (RF) communication can be used to eliminate the need for, or in addition to, dial-in telephone access.

In addition to the collection and transmission of data related to the operation of the device and/or the patient's health, system management features are also provided. In this way the distribution of the collected data and any reports and analysis can be performed through the internet or the dedicated communications lines to remote computers used by the prescribing physicians or their staff. Thus, for example, if a physician requires either a second opinion or further review of specific data, that data can be retransmitted to another caregiver for the proper analysis and consultation between health care professionals. Analysis of equipment performance data may indicate the need for service or repair, which a database type gathering of information would allow maintenance personnel to observe trends and provide analysis for preventive service actions, not only of a particular monitoring device but any and all devices which may be in use in the field. Analysis of patient data and the results of any remote analysis allow the prescribing physician to adjust treatments or therapies, either through updating tile operation of the device by changing the software via the internet or by prescribing different medicines and notifying the patient that a different prescription is already waiting and available for him or her for delivery. Since the data is continually collected, the physician can analyze the compliance and use data to allow intervention by the prescribing physician if the device is not being used by the patient or is being used improperly.

In addition, the device parameters or software for the patient-worn medical device can be updated automatically when contact is made by the patient for the periodic data download to the central location. This update may be specific to the particular patient and occur at the direction of the prescribing physician after review of performance and patient data. This update may also be of the general update type which is applied to all devices in the field. The data collected from the patient may be used to preprogram replacement devices prior to being sent to particular patients, so that there is no need for the patient to return to the dispensing center, physician's office, hospital or pharmacy, etc. if service of the device is required. In the event that a device problem requires regulatory action or recall, these systems can be easily located since the continual analysis of patient compliance and use data allows for automatic equipment tracking. These systems may be automatically located through the central data location and can be either updated, disabled remotely when contact is established or the patient can be notified that a recall is in effect and needs to return to the dispensing center as soon as possible. In addition to allowing action to be taken more quickly, the operational status of individual systems may be tracked. By continually monitoring the proper use of the devices, the dispensing center procedures can be continually updated for purposes such as billing and continual monitoring of the device to ensure that the physician's instructions are being fully complied with.

Since each of the parties (patients, physicians, maintenance personnel and equipment manufacturer) can access the data on an as needed basis, correct operation and use by the patient can be ensured. By continually monitoring patient's data, for example, if a physician determines that certain anomalies continue to occur in different monitors provided to different patients, the physician can check with maintenance personnel and those personnel can access the data to ensure that it is the equipment that may not be operating correctly and not that each patient is encountering the exact same medical condition simultaneously. This type of trend analysis is helpful in both providing proper patient care as well as providing a device which is most effective for monitoring and treating these patients. Thus the freedom that the patient enjoys by having a patient-worn device is increased by eliminating endless trips to and from the dispensing center to both check the health of the patient and for routine maintenance which again can be done from a remote location.

As shown in FIG. 1, the data collection and system management design of the present invention allows the various concerned persons to have access to the central location, such as a web server, for the exchange of data and information. The Internet serves as a "gateway" for enabling each of the parties to be linked across the information network. The modem, or other data transfer technology, used as part of the wearable medical device can dial into a central location, such as an Internet operated, for example, by the assignee of the present invention, by means of a communication server. Multiple party access to the host location by patients can be provided by a modem bank.

At the central location host, a searchable database, such as an SQL Database, can be provided to allow for performance analysis and post-market analysis of the overall operation of all of the patient-worn medical devices. For example, device technicians and engineers can search for error trends or other operational characteristics of the device to monitor proper operation of the medical devices. Alternatively, if any particular device has returned an error or other message to the central location, a technician can analyze the operation of that device and either recommend a course of action for the patient to correct the problem, transmit software instructions directly to the device to upgrade its operation, or instruct the patient to return the device to the distribution center for a properly operating machine. Broadcast messages may also be sent to all the devices for implementing these actions should a generic problem or fault be detected in the operation of the mechanism.

At the caregiver or doctor's office, the patient's physician can periodically review any particular patient's data by logging onto the central location, using a conventional web browser such as Netscape Navigator or Microsoft Internet Explorer. Once the appropriate password or other security procedures have been undertaken, the physician can download patient data for medical analysis, such as a periodic review of ECG data, or for specific review of a detected arrhythmia event or other machine implemented therapeutic action. After analysis of the patient medical data, the physician can prescribe remedial action for the patient in a variety of ways. This can be accomplished by means of electronic data transmission to the patient at the next scheduled data download, an instantaneous message to the patient indicating an immediate course of action, or even dispatching emergency personnel to the patient's home. The physician can also contact the central location host in the event that there is a concern with the proper operation of any of the devices. Even in those situations where the physician is not physically located at his or her office, by using a communication network such as the Internet the physician can obtain access to patient data, especially in an emergency situation, from virtually anywhere in the world. Another advantage to this remote access capability is that a physician can consult with a specialist, by either granting that person access to the data or retransmitting the data directly to the specialist over the Internet, such that all the parties can have access to the data simultaneously. Alternatively, a web-based conference can be conducted by persons located at various locations by each of the parties accessing the same secure website to analyze the data.

Figure 2:
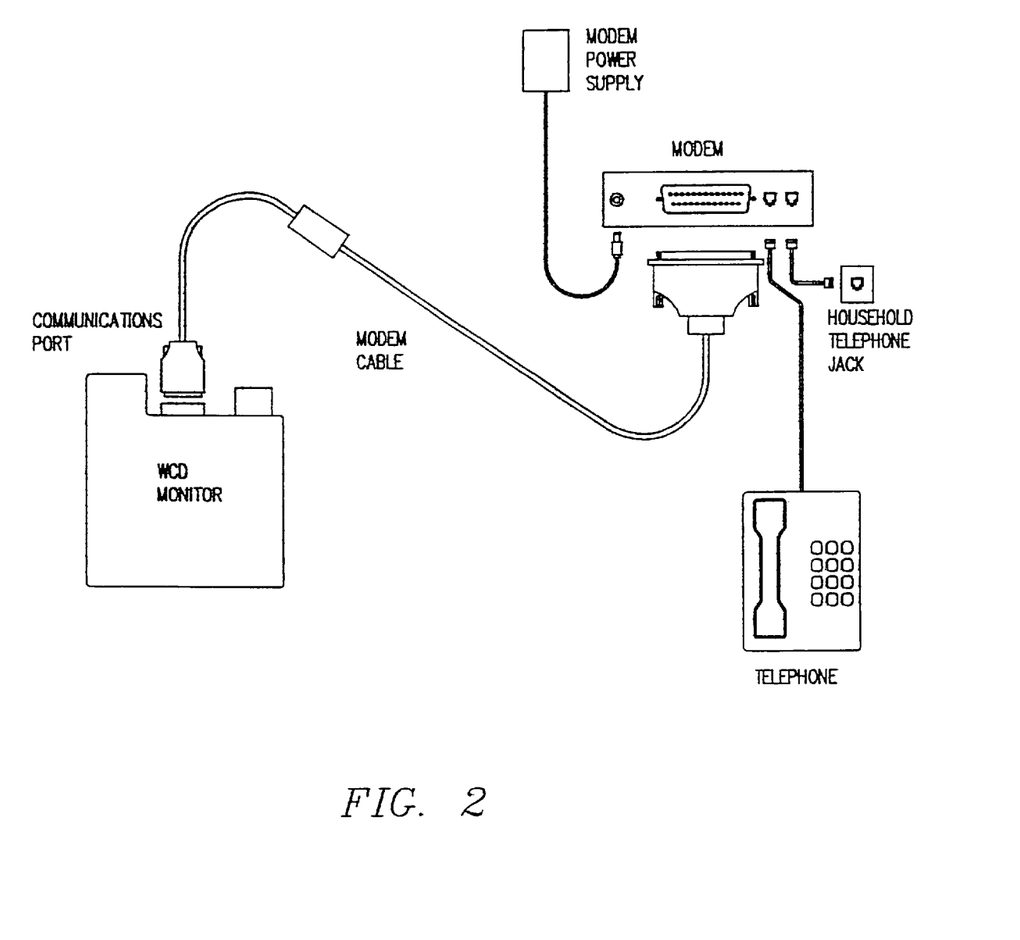
FIG. 2 is a schematic representation of one embodiment of a means for connecting a wearable medical device with a communications network.
Figure 3A:
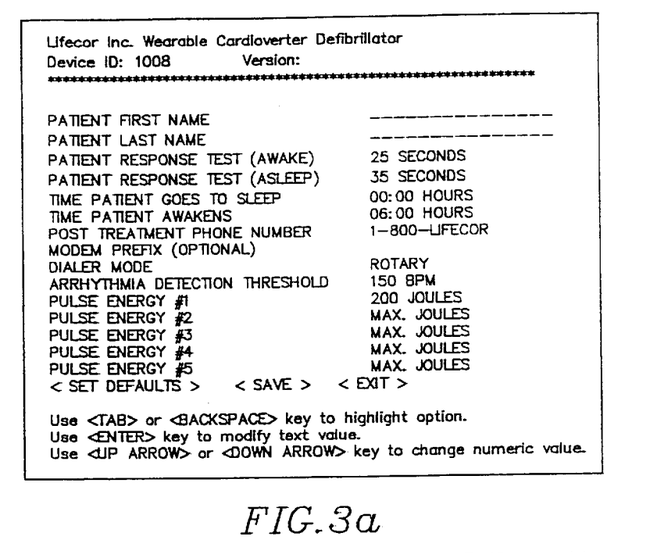
Figure 3B:
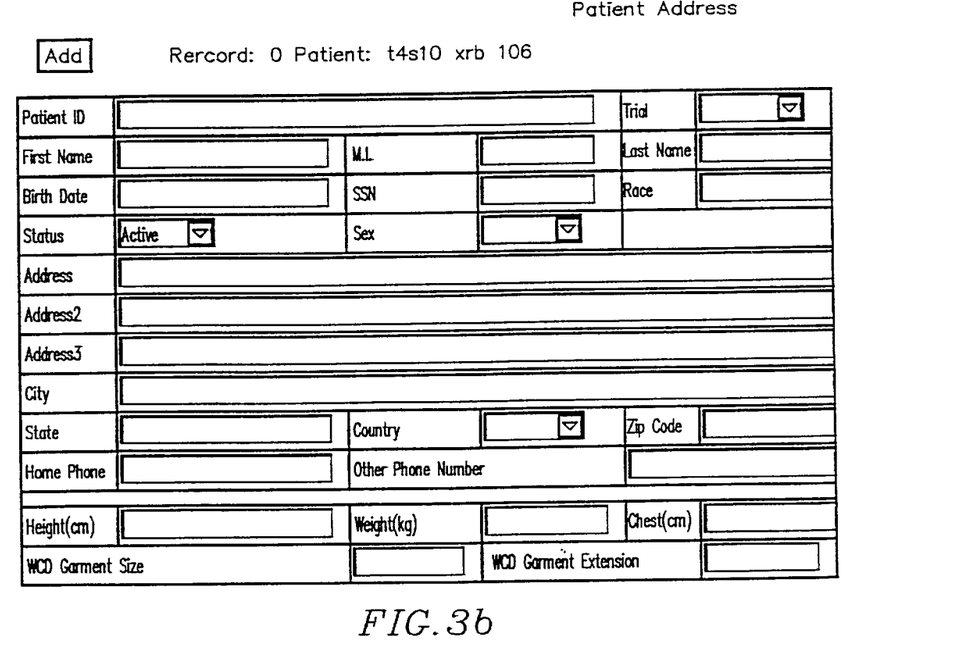

In order to prepare a wearable cardiac defibrillator monitor (WCD) to transmit information over the internet or other communications network, it must first be programmed to include the specific patient information. The WCD in order to perform this initial program, the following steps are performed:

The WCD must first be connected to a personal computer (PC) in order to program the initial patient information. This is done by use of a computer cable which connects the monitor to a serial port for example of the PC. This is shown in FIG. 2. A program is initiated on the PC which will then program the information into the computer memory of the defibrillator monitor. When setting up a new patient, the current time and date are entered into the WCD monitor. When configuring the monitor for a new patient, a "set-up new patient" operation is performed. The monitor is programmed with the patient's full name, which can then be used when transmitting data to identify the patient directly. When the patient information is entered, the particular patient settings for that patient are then input into the monitor's memory. As shown in FIG. 3, there are numerous data points that must be inputted. On-screen instructions inform the service provider as to how to modify the particular patient data. Some of these parameters may include whether or not a modem prefix is required to dial from a patient's residence or whether the phone is digital (tone) or rotary (pulse).

After these initial patient parameters are installed, the patient baseline ECG data is inputted into the monitor.

The monitor must first be disconnected from the PC by disconnecting the computer cable from the monitor. The patient is at this time wearing the monitor such that the electrodes are placed on the appropriate spots on the patients body. The monitor is then activated to record patient's baseline ECG which will be displayed on the monitor. Generally, the monitor will record the patients heart rhythm for a period of from 45 seconds to 5 minutes to initialize, as the monitor device learns the patient's baseline. Once the monitor has performed this function a message is displayed which states that the baseline recording is complete and that the monitor can begin normal functioning. In the event that the patient has a rhythm that is difficult to learn, the monitor provides a message such as "baseline failed" and patient baseline recording can begin again. In the event that the electrodes are not properly placed on the patient's body, a message is displayed which informs the user to properly position the electrode belt for the wearable defibrillator.

Once the patient's baseline information has been recorded, this information must then be sent to the device manufacturer's database server via the modem.

The WCD system also includes a modem cable for connecting the monitor to an external modem. Alternatively, an internal modem may be provided in the monitor. The appropriate phone lines are connected and the modem is connected to the phone line and/or a common household telephone jack. When the telephone connections have been made, the modem is connected to the power supply and turned on to begin the information transfer. Preferably, the patient's database resides on the Lifecor's internet database server to receive the various patient information. When the modem and monitor are properly connected a message is displayed to indicate that it is permissible to now send data. The patient can then initiate data transfer by pressing the appropriate button on the monitor such that the modem begins dialing into the data center's database server. During data transfer, a message is displayed that such data transfer is in progress. When transfer is complete, the appropriate message is displayed indicating that the data transfer is complete and that modem should now be disconnected. In the event of any problem with the data transfer, a message is displayed and a further attempt to transmit data should be performed. Upon successful transfer of data the monitor is disconnected from the modem.

Once the patient information has been baselined and the monitor information has been sent via modem to the Lifecor database server or other communications network data center, the internet can then be used to enter and/or review patient data. When entering this website, a user is prompted to enter their login name and password in order to enter the "WCDNET". Upon successfully entering the website, a patient list is displayed to the user such that patient information can be accessed in several ways. Patients can either be accessed directly by patient name or by an identified category such as patient identification, last name, first name or serial number of the device, and a search function performed. For example, if the patient's name begins with the letter R, this can be inputted into the appropriate area on the patient's record and a search done for all patient's who last name begin with the letter R. Once the desired patient is selected, the patient screen is displayed. This allows the user to enter more patient information such as address, phone number, height, weight, chest circumference, and garment and extension size for the WCD monitor belt. Once this information is inputted, it is saved within the communications network data center or database server. Next, appropriate patient demographic and medical information can be inputted. A typical screen display for inputting various patient information is shown in FIG. 3. Once the entire patient initial information is inputted, this data is saved to be compared against later downloads of information from that patient.

Figure 4:
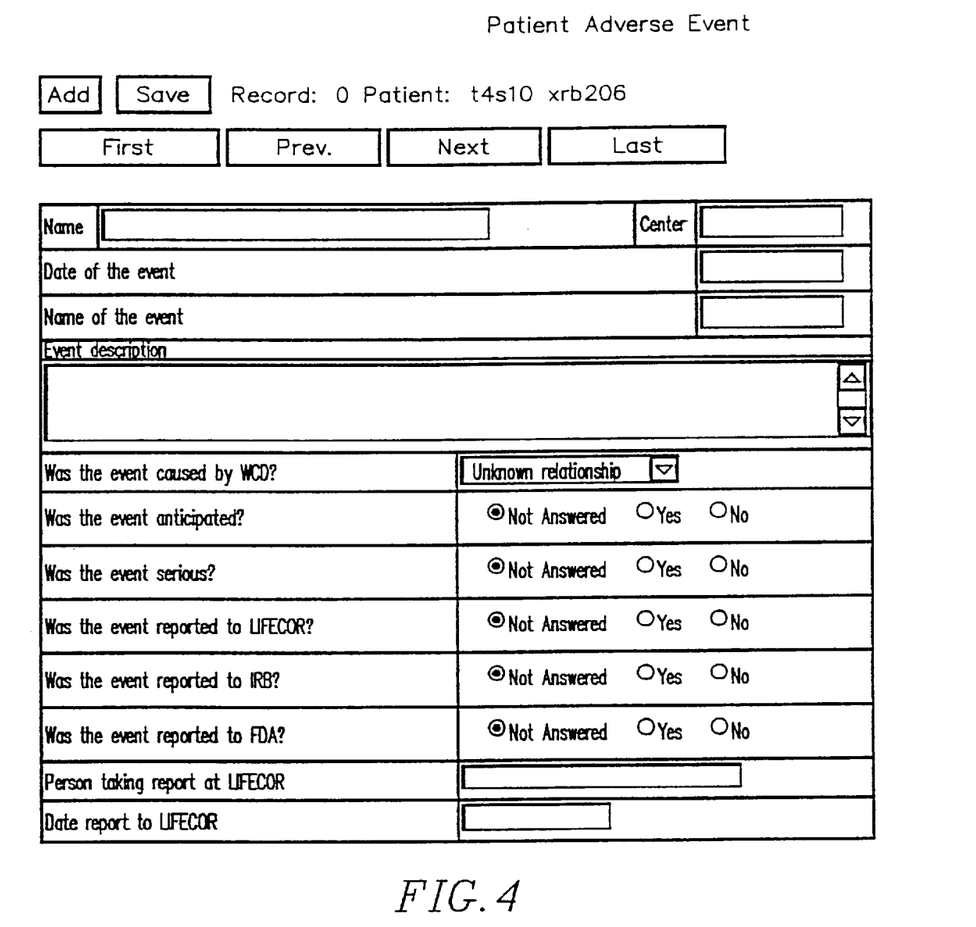
FIG. 4 is a representation of a screen display indicating a patient adverse event as recorded by a wearable medical device.

Should an "adverse event" occur, such a screen is also provided for the health care provider to input the pertinent information, as shown in FIG. 4. These include the date of the adverse event, nature or description of the event, and other event information.

Figure 5:
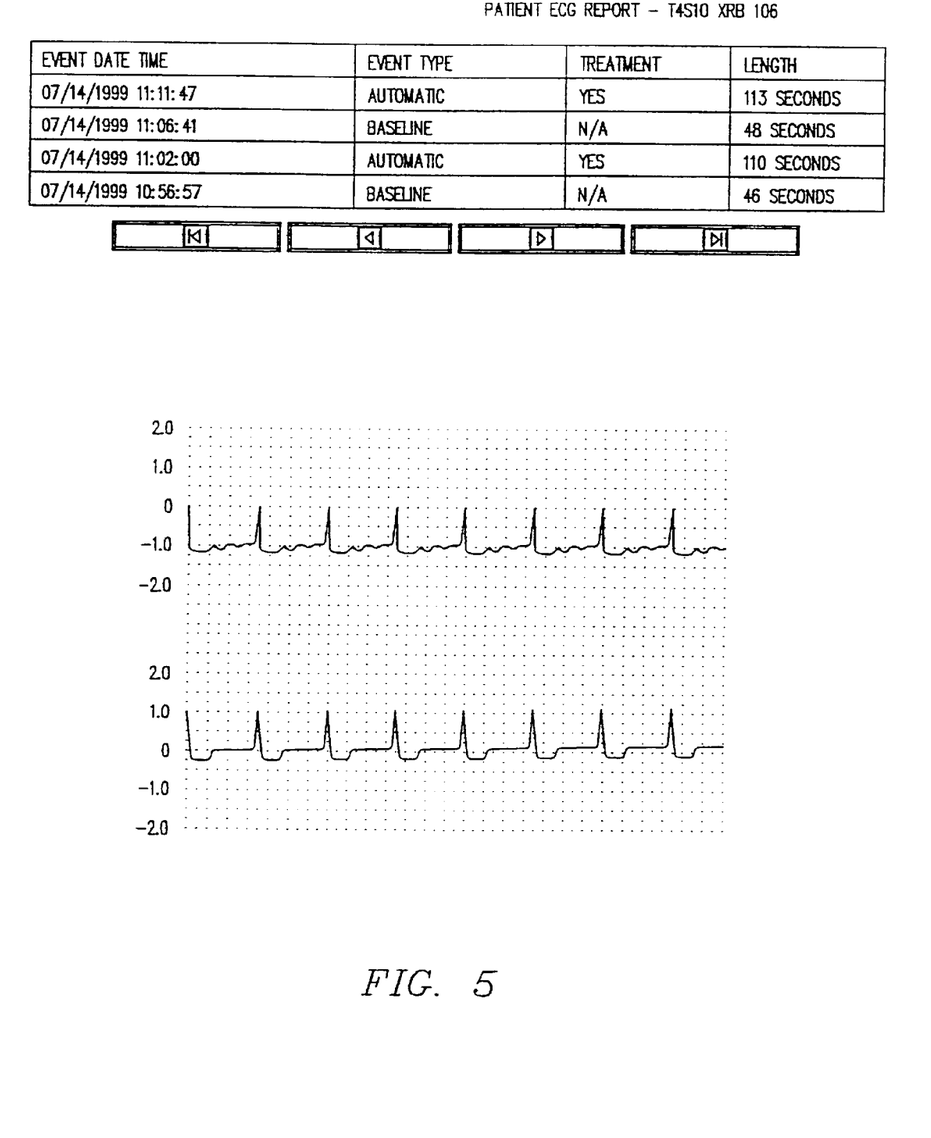
FIG. 5 is a representation of a screen display showing an ECG report for a wearable cardiac defibrillator.

In order to view the patient's electrocardiogram (ECG) recordings, the "ECG report screen" as shown in FIG. 5 is accessed. The ECG recording are listed by date, time, type, treatment (if applicable) and length.

Figure 6:
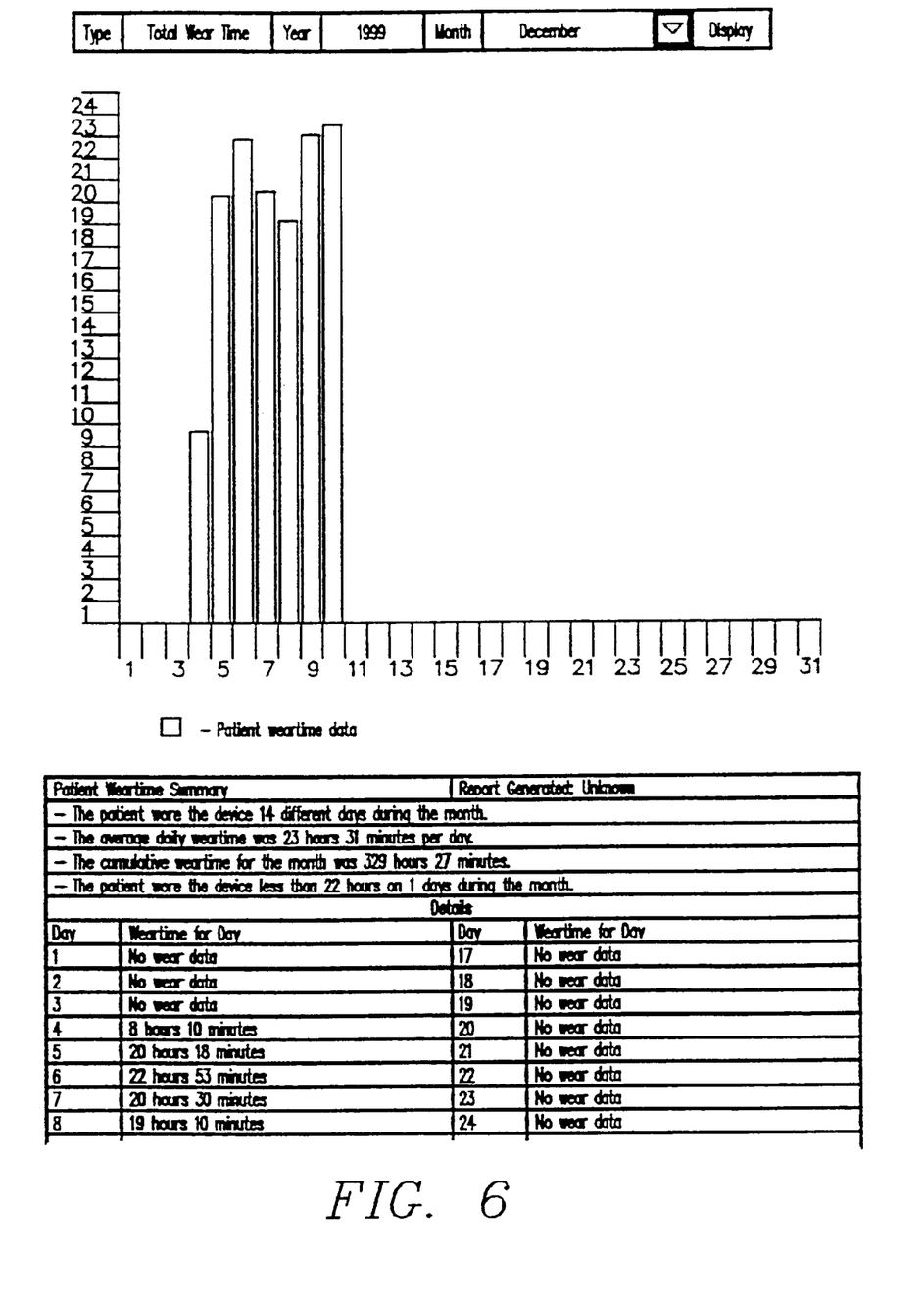
FIG. 6 is a representation of a screen display for monitoring correct patient use of the wearable medical device.

To see the patient's compliance record, the "compliance screen" as shown in FIG. 6 is accessed. This shows for example, how many hours out of each day the patient has actually been wearing the monitor such that data is being inputted into the system.

In order to provide the patient information into the Lifecor's internet site database, the patient is prompted periodically, such as in the order of every 7 days, to connect his/her monitor to the modem for transfer of information to the database. The message is displayed indicating that it is time to connect to the modem to transfer the data to the database server. This communication is performed as set forth above.

The monitor records electrocardiogram data which is to be sent to the monitoring service. The patient is thus prompted to transfer this data to the physician so that active monitoring of the patient by a health care provider can be performed.

During such data transfers there are to be updates to the patient's monitoring device, which will be readily apparent with the patient's device serial number or other identifying data is also transmitted with that patient's data, additional instructions can be sent from the Lifecor's web site to the patient's monitor. This may include, for example, software updates for the monitor, as well as alerting the patient to product recalls, if necessary, instructing the patient to return the monitor to the health care service provider for additional onsite maintenance and upgrading of the hardware of the device.

For an implantable device, a transcutaneous transmitter is used to communicate with the implanted medical device; such as a pacemaker. Operating parameters can be updated, such as these previously described above according to the unique operating characteristics of the implanted device within a particular patient. As the patient's medical information is analyzed from time to time by a physician, these operating parameters can be adjusted in order to more fully serve the patient's medical needs. For a pacemaker, for example, the transcutaneous transmitter can be placed over the area on the patient's body where the device is implanted, and radio frequency (RF) communications between the pacemaker and the transmitter can be established. The transmitter is in turn operatively associated with global communication network, such as with a base station having a modem and other communication hardware as is well known in the art.

Additionally, the wearable device may also communicate with the network via a base station. Rather than having to remove the wearable device or directly plug it into the communication device, and RF or infrared communication link can be used. In this way, should the device detect an emergency situation, especially when the patient is asleep or unconscious, the device can automatically establish a communication link with the physicians office, for example, or call emergency personnel directly to the patient's location.

Therefore, the present invention provides distinct and unique advantages for the patient-worn medical devices by integrating data collection and system management functions into a central location for the proper operation of these devices. And while specific embodiments of practicing the invention have been described in detail, it will be appreciated by those skilled in the art that various modifications and alternatives to those details could be developed in light of the overall teaching of the disclosure. Accordingly, the particular arrangements disclosed are meant to be illustrative only and not limiting to the scope of the invention which is to be given the full breadth of the foregoing description and appended claims and any and all equivalents

We claim:

1. A method of monitoring patient medical information for the treatment of a patient, the method comprising the steps of:

providing a wearable medical device for monitoring patient medical information and treating the patient in response to a monitored medical condition;

operatively connecting the medical device to the patient such that the medical device is worn by the patient;

recording the patient medical information in a storage means of the medical device;

operatively connecting the medical device to a communications system;

transmitting the patient medical information to a health care provider by means of said communications system and recording the patient medical information in an information database; and providing access to the patient medical information to individuals.

2. A method of monitoring patient medical information for the treatment of a patient, the method comprising the steps of:

providing a wearable medical device for treating the patient and monitoring patient medical information;

operatively connecting the medical device to the patient such that the medical device is worn by the patient;

recording the patient medical information, device performance data and patient compliance data in a storage means of the medical device;

operatively connecting the medical device to a communications system;

transmitting the patient medical information, device performance data and patient compliance data to a health care provider by means of said communications system and recording the patient medical information, device performance data and patient compliance data in an information database, wherein said transmitting step is performed while the medical device is operatively connected to the patient for providing treatment to the patient; and providing access to the patient medical information, device performance data and patient compliance data to individuals.

3. The method as set forth in claim 2, wherein the medical device is a cardiac defibrillation device and the step of recording the patient medical information comprises recording electrocardiograms of the patient's heart rhythm.

4. A system for monitoring patient medical information and providing treatment to a patient, the system comprising:

a wearable medical device for monitoring and storing medical parameters and treating the patient in response to a monitored medical condition, the medical device operatively attachable to the patient such that the medical device is worn by the patient;

a communications network;

means for connecting the medical device to the communication network;

a patient database;

means for monitoring and storing operations information of the medical device and patient compliance and use data;

means for connecting the patient database to the communication network; and means for exchanging information between the medical device and the patient database, including means for transmitting the medical device operations information and the patient compliance and use data to the patient database via the communication network.

5. The system as recited in claim 4, further comprising means for monitoring an operating status of the medical device.

6. The system as recited in claim 5 wherein the medical device is a cardiac defibrillator and said medical parameters include at least partial electro-cardiogram (ECG) data.

7. The system as recited in claim 4, wherein the medical device is a wearable cardio-defibrillator.

8. The system as recited in claim 4, wherein said means for exchanging information includes means for transmitting patient medical information from the medical device to the patient database.

9. The system as recited in claim 4, wherein said means for monitoring operations information includes means for monitoring battery status for a battery of the medical device.

10. The system as recited in claim 6, further comprising means for storing operating status information of the cardiac defibrillator and wherein said means for exchanging information includes means for transmitting operating status information to the patient database via the communication network.

11. The system as recited in claim 10 wherein said means for monitoring operating status information includes means for monitoring battery status for a battery of the medical device.

12. The system as recited in claim 11 wherein said means for monitoring operating status information further includes means for transmitting the operating status information to the patient database.

13. The system as recited in claim 12, wherein said operating status information includes one or more of battery capacity, system memory, patient device utilization and system noise.

14. The system as recited in claim 13, further including means for analyzing said operating status information.

15. The system as recited in claim 14, further including means for transmitting parameter update information to the medical device based on said analysis of the operating status information.

16. The system as recited in claim 8, further including means for accessing the patient database via the communication network, wherein medical personnel can analyze the patient medical information from a remote location.

17. The system as recited in claim 10, further including means for accessing the patient database via the communication network, such that technical personnel can analyze said operating status information.

18. The system as recited in claim 17, wherein said operating status information includes one or more of patient wear data for the cardiac defibrillator, alarm indicators, and ECG signal information.

19. A system for monitoring patient medical information and providing treatment to a patient, the system comprising:

a wearable medical device for monitoring and storing medical parameters and treating the patient in response to a monitored medical condition, the medical device operatively attachable to the patient such that the medical device is worn by the patient;

a communications network;

means for connecting the medical device to the communication network;

a patient database;

means for connecting the patient database to the communication network;

means for monitoring and storing patient medical parameters, device performance data and patient compliance data;

means for exchanging information between the medical device and the patient database, including means for transmitting the patient medical parameters, device performance data and patient compliance data to the patient database via the communications network; and means for downloading device parameter software to the medical device from the communications network.

20. The system as recited in claim 19, wherein the device parameter software includes one or more of operations upgrade software, patient compliance guidelines or product maintenance information.

21. A system for monitoring patient medical information and providing treatment to a patient, the system comprising:

a wearable cardiac defibrillator for collecting and storing electro-cardiogram (ECG) data and treating the patient in response to the collected ECG data, the cardiac defibrillator operatively attachable to the patient such that the cardiac defibrillator is worn by the patient;

a communications network;

means for connecting the cardiac defibrillator to the communication network;

a patient database;

means for connecting the patient database to the communication network;

means for monitoring and storing patient medical parameters, device performance data and patient compliance data;

means for exchanging information between the cardiac defibrillator and the patient database, including means for transmitting the patient medical parameters, device performance data and patient compliance data to the patient database via the communications network, and means for transmitting instructions on proper use and operation of the cardiac defibrillator to the patient via the communications network; and means for downloading software to the cardiac defibrillator from the communications network.

22. A system for monitoring patient medical information and providing treatment to a patient, the system comprising:

a wearable cardiac defibrillator for collecting and storing electro-cardiogram (ECG) data and treating the patient in response to the collected ECG data, the cardiac defibrillator operatively attachable to the patient such that the cardiac defibrillator is worn by the patient;

a communications network;

means for connecting the cardiac defibrillator to the communication network;

a patient database;

means for connecting the patient database to the communication network;

means for exchanging information between the cardiac defibrillator and the patient database; and means for downloading instructions for proper operation of the cardiac defibrillator to a patient wearing the cardiac defibrillator via the communications network.

23. The system as recited in claim 22, wherein said means for connecting the cardiac defibrillator to the communications network comprises a base station having a modem for accessing the communications network and a transcutaneous informational transmission device operably associated with the base station for communication with the cardiac defibrillator.

24. The system as recited in claim 22, further comprising means for monitoring an operating status of the cardiac defibrillator.

25. The system as recited in claim 22, wherein said means for exchanging information includes means for transmitting patient medical information from the cardiac defibrillator to the patient database.

26. The system as recited in claim 22, wherein said means for monitoring operations information includes means for monitoring battery status for a battery of the cardiac defibrillator.

27. The system as recited in claim 24, further comprising means for storing operating status information of the cardiac defibrillator and wherein said means for exchanging information includes means for transmitting operating status information to the patient database via the communication network.

28. The system as recited in claim 27 wherein said means for monitoring operating status information includes means for monitoring battery status for a battery of the cardiac defibrillator.

29. The system as recited in claim 28 wherein said means for monitoring operating status information further includes means for transmitting the operating status information to the patient database.

30. The system as recited in claim 29 wherein said operating status information includes one or more of battery capacity, system memory, patient device utilization and system noise.

31. The system as recited in claim 30, further including means for analyzing said operating status information.

32. The system as recited in claim 31, further including means for transmitting parameter update information to the cardiac defibrillator based on said analysis of the operating status information.

33. The system as recited in claim 25, further including means for accessing the patient database via the communication network, wherein medical personnel can analyze the patient medical information from a remote location.

34. The system as recited in claim 27, further including means for accessing the patient database via the communication network, such that technical personnel can analyze said operating status information.

35. The system as recited in claim 34, wherein said operating status information includes one or more of patient wear data for the cardiac defibrillator, alarm indicators, and ECG signal information.

* * * * *

Disclaimer

6,681,003 B2 - Marshal Linder, Pittsburgh, PA (US); Thomas Kaib, North Hunningdon, PA (US). DATA COLLECTION AND SYSTEM MANAGEMENT FOR PATIENT-WORN MEDICAL DEVICES. Patent dated January 20, 2004. Disclaimer filed December 23, 2016, by the assignee, inventors.

I hereby disclaim the following complete claims 1 of said patent.

*(Official Gazette, July 19, 2022)*